United States Patent [19]

Angelastro et al.

[11] Patent Number: 5,510,333

[45] Date of Patent: Apr. 23, 1996

[54] INHIBITORS OF CATHEPSIN G AND ELASTASE FOR PREVENTING CONNECTIVE TISSUE DEGRADATION

[75] Inventors: Michael R. Angelastro; Philippe Bey, both of Cincinnati, Ohio; Niall S. Doherty, Stonington, Conn.; Michael J. Janusz, Oregonia, Ohio; Shujaath Mehdi; Norton P. Peet, both of Cincinnati, Ohio

[73] Assignee: Merrell Pharmaceuticals Inc., Cincinnati, Ohio

[21] Appl. No.: 462,456

[22] Filed: Jun. 5, 1995

Related U.S. Application Data

[63] Continuation of Ser. No. 342,999, Nov. 21, 1994, abandoned, which is a continuation of Ser. No. 222,552, Apr. 4, 1994, abandoned, which is a continuation of Ser. No. 987,587, Dec. 8, 1992, abandoned, which is a continuation of Ser. No. 704,499, May 23, 1991, abandoned.

[51] Int. Cl.$^6$ .............. A61K 38/07; A61K 38/08
[52] U.S. Cl. .............. 514/18; 530/323; 530/328; 530/329; 530/330; 435/218; 435/219; 514/2; 514/16; 514/17
[58] Field of Search .............. 435/218, 219; 514/2, 16–18; 530/323, 328, 329, 330

[56] References Cited

U.S. PATENT DOCUMENTS

| | | | |
|---|---|---|---|
| 4,485,100 | 11/1984 | Hochstrasser et al. | 514/12 |
| 4,629,724 | 12/1986 | Ryono et al. | 514/18 |
| 4,636,489 | 1/1987 | Seemüller et al. | 514/12 |
| 4,643,991 | 2/1987 | Digenis et al. | 514/18 |
| 4,873,221 | 10/1989 | Trainor | 514/18 |
| 4,880,780 | 11/1989 | Tranor et al. | 514/18 |
| 4,910,190 | 3/1990 | Bergeson et al. | 514/19 |
| 5,055,450 | 10/1991 | Edwards et al. | 514/19 |
| 5,061,691 | 10/1991 | Yagi et al. | 514/17 |

FOREIGN PATENT DOCUMENTS

| | | |
|---|---|---|
| 0195212 | 9/1986 | European Pat. Off. . |
| 0275101 | 7/1988 | European Pat. Off. . |
| 0356595 | 3/1990 | European Pat. Off. . |
| 0363284 | 4/1990 | European Pat. Off. . |
| 0410411 | 1/1991 | European Pat. Off. . |
| 3938971 | 5/1991 | Germany ............ C07K 7/10 |

OTHER PUBLICATIONS

Powers et al; *Pulmonary Emphysema and Proteolysis* pp. 41–48 (1986).
Hornebeck et al; Cell Biochemistry and Function 5:113–122 (1987).
Johnson et al; J. Biol. Chem. 253(20):7142–4 (1978).
Nakajima et al; J. Biol. Chem. 254(10):4027–32 (1979).
Martodam et al; PNAS (USA) 76(5):2128–32 (1979).
McRae et al; Biochemistry 19:3973–8 (1980).
Reilly et al; Biochim. Biophys. Acta 621:147–57 (1980).
Ponpipom et al; J. Med. Chem. 24:1388–95 (1981).
*The Merck Manual;* 15th Ed. Berkow et al; Eds. pp. 620–623; 636–643 (1987).
Hornebeck et al; Chemical Abstracts 107:196313z (1987).
Poners et al; Chemical Abstracts 108:33954r (1988).
Drinkwater et al; J. Biol. Chem. 263(18):8565–68 (1988).
McWherter et al; Biochem. 28:5708–14 (1989).
Baba et al; J. Biol. Chem. 264(20):11920–7 (1989).
Rao et al; J. Biol. Chem. 266(15):9540–8 (1991, May 1975).
Tsubol et al; Chemical Abstracts 115:44919d (Aug. 5, 1991).
Steinmeyer et al; Arzneim.–Forsch./Drug Res. 41[I], 1:77–80 (1991).
Hassall et al, *Febs Lett*, 183, 201–205, (1985).
Fletcher et al, *Am. Rev. Respir. Dis.*, 141, 672–677, (1990).
Malech et al, *New Engl. J. Med.*, 317, 687–694 (1987).
Snider, *Eur. J. Respir. Dis.*, 69, (Suppl 146) 17–35, (1986).
Shah et al, *J. Med. Chem.*, 35, 3745–3754, (1992).
Peet, et al, *J. Med. Chem.*, 33, 394–407, (1990).
Angelastro et al, *Bioorg. Med. Chem. Lett*, 3, 525–530, (1990).
Mehdi, *Bioorg. Chem.*, 21, 249–259, (1993).
Mehdi, S. et al., *Biochemical and Biophysical Research Communications*, vol. 166, No. 2, pp. 595–600 (1990).
Rice, W. G. et al., *Science*, vol. 249, pp. 178–181 (1990).

*Primary Examiner*—Douglas W. Robinson
*Assistant Examiner*—Kathleen Kahler Fonda
*Attorney, Agent, or Firm*—William R. Boudreaux

[57] ABSTRACT

Novel compounds which are chemically linked inhibitors of the proteases Elastase and Cathepsin G prevent connective tissue degradation associated with neutrophil induced inflammatory disease.

10 Claims, No Drawings

INHIBITORS OF CATHEPSIN G AND ELASTASE FOR PREVENTING CONNECTIVE TISSUE DEGRADATION

CROSS-REFERENCE TO RELATED APPLICATION

This is a continuation of application Ser. No. 08/342,999, filed Nov. 21, 1994 now abandoned, which is a continuation of application Ser. No. 08/222,552 filed Apr. 4, 1994 now abandoned which is a continuation of application Ser. No. 07/987,587 filed Dec. 8, 1992 now abandoned which is a continuation of application Ser. No. 07/704,499 filed May 23, 1991 now abandoned which is herein incorporated by reference.

This invention relates to novel chemical compounds useful for preventing connective tissue degradation associated with neutrophil associated inflammatory disease.

BACKGROUND OF THE INVENTION

Human neutrophil elastase and cathepsin G have been implicated in the tissue destruction associated with a number of inflammatory diseases such as chronic bronchitis, cystic fibrosis, and rheumatoid arthritis. H. L. Malech and J. I. Gallin, New Engl. J. Med., 317(11), 687 (1987). Both elastase and cathepsin G have a broad range of proteolytic activity against a number of connective tissue macromolecules including elastin, fibronectin, collagen, and proteoglycan. The presence of these enzymes may contribute to the pathology of these diseases.

Normal plasma contains large quantities of protease inhibitors that control a variety of enzymes involved in connective tissue turnover and inflammation. For example, $\alpha$-1-antiprotease ($\alpha$-1-PI) is a serine protease inhibitor that blocks the activity of both elastase and, at a slower rate, cathepsin G. $\alpha$-1-PI has received considerable interest because reduction in plasma levels to less than 15% of normal is associated with the early development of emphysema.

In addition to plasma derived protease inhibitors, secretory fluids, including bronchial, nasal, cervical mucus, and seminal fluid contain an endogenous protease inhibitor called secretory leukoprotease inhibitor (SLPI) that can inactivate both elastase and cathepsin G and is believed to play an important role in maintaining the integrity of the epithelium in the presence of inflammatory cell proteases. In certain pathological states $\alpha$-1-PI and SLPI are inactivated by neutrophil oxidative mechanisms allowing the neutrophil proteases to function in an essentially inhibitor-free environment. For example, bronchial lavage fluids from patients with adult respiratory distress syndrome (ARDS) have been found to contain active elastase and $\alpha$-1-PI that had been inactivated by oxidation.

In addition to oxidative mechanisms, neutrophils possess non-oxidative mechanisms for eluding inhibition by antiproteases. Neutrophils from patients with chronic granulomatous disease are capable of degrading endothelial cell matrices in the presence of excess $\alpha$-1-PI. There is considerable in vitro evidence that stimulated neutrophils can tightly bind to their substrates such that serum antiproteases are effectively excluded from the microenviroment of tight cell-substrate contact. The influx of large numbers of neutrophils to an inflammatory site may result in considerable tissue damage due to the proteolysis that occurs in this region.

Applicants have determined that elastase and cathepsin G are the primary neutrophil proteases responsible for cartilage matrix degradation as measured by the ability of neutrophil lysate, purified elastase and cathepsin G, and stimulated neutrophils to degrade cartilage matrix proteoglycan. Further, applicants have discovered that stimulated neutrophils degrade cartilage matrix in the presence of serum antiproteases indicating that degradation occurs in the serum-protected pericellular area between the neutrophils and substrate. Degradation of cartilage matrix occurring in the pericellular region could be blocked only by inhibiting both elastase and cathepsin G. Applicants have discovered a class of enzyme inhibitors which inhibit both elastase and cathepsin G and are thus useful in preventing neutrophil mediated connective tissue degradation.

SUMMARY OF THE INVENTION

Compounds of the formula

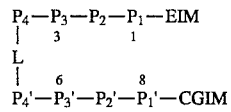

(SEQ ID NO: 1)

wherein $P_1$ is Ala, bAla, Leu, Ile, Val, Nva, bVal, Met, Nle, Gly, or Sar;

$P_1'$ is Ala, bAla, Leu, Ile, Val, Nva, bVal, Met, Nle, Phe, Tyr, Tyr(Me), Ala(3pyr), Ala(4pyr), Trp, or Nal(1);

$P_2$ is Pro, Ind, Ala, bAla, Leu, Ile, Val, Nva, bVal, Met, Nle, Phe, Tyr, Tyr(Me), Ala(3pyr), Ala(4pyr), Trp, or Nal(1);

$P_2'$ is Pro, Ind, Ala, bAla, Leu, Ile, Val, Nva, bVal, Met, Nle, Gly, Sar or is absent;

$P_3$ is Lys, Arg, Pro, Ind, Ala, bAla, Leu, Ile, Val, Nva, bVal, Met, or Nle;

$P_3'$ is Ala, bAla, Leu, Ile, Val, Nva, bVal, Met, Nle, Gly, Sar or is absent;

$P_4$ is Ala, bAla, Leu, Ile, Val, Nva, bVal, Met, Nle, or is absent;

$P_4'$ is Ala, bAla, Leu, Ile, Val, Nva, bVal, Met, Nle, Gly, Sar, or is absent;

L is a group of one of the formulae

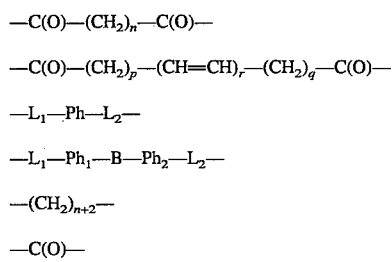

wherein n is 0 or an integer of from 1 to 6;

p and q are each independently an integer of from 1 to 6;

r is 1 or 2;

$L_1$ and $L_2$ are each independently selected from a carbonyl or sulfonyl group wherein $L_1$ is bound to the elastase inhibiting fragment and $L_2$ is bound to the cathepsin G inhibiting fragment;

Ph, Ph$_1$, and Ph$_2$ are each independently a m-phenylene or p-phenylene group;

B is a bond, —(CH$_2$)$_m$—, or a —S(O)$_2$N(H)C(O)— group;

EIM and CGIM are each independently selected from the group consisting of —C(O)C(O)R, —CF$_2$CF$_3$, —CF$_3$, —CF$_2$H, —CO$_2$R$_3$, —CONHR$_3$, —CF$_2$CHR$_3$C(O)NHR, —H, alkyl, aryl, aralkyl, —C(O)R, wherein R$_3$ is H, alkyl, phenyl, benzyl, R is OH or alkoxy or a pharmaceutically acceptable salt thereof are useful in the prevention of cartilage degradation.

DETAILED DESCRIPTION OF THE INVENTION

Isosteres of the compounds of formula I include those wherein (a) one or more of the α-amino acid residues of the R$_1$ substituent is in its unnatural configuration (when there is a natural configuration) or (b) when the normal peptidic amide linkage is modified, such as for example, to form —CH$_2$NH—(reduced), —COCH$_2$—(keto), —CH(OH)CH$_2$—(hydroxy), —CH(NH$_2$)CH$_2$—(amino), —CH$_2$CH$_2$—(hydrocarbon). Preferably a compound of the invention should not be in an isosteric form; particularly it is preferred that there be no modified peptidic amide group in the R$_1$ group, but if there is, it is preferable to keep the isosteric modifications to a minimum.

Unless otherwise stated, the α-amino acid building blocks of these peptidase substrate analogs are preferably in their L-configuration. As is conventional nomenclature used by peptide chemists, the code for an amino acid wherein the first (or other) letter of the code is upper case indicates that the amino acid has the natural "L" configuration and wherein the first (or other) letter of the code is lower case indicates that the amino acid has "D" configuration. Throughout this specification reference will be made to lower case amino acid codes or codes proceeded by "(D)-" and these shall both be taken as equivalent.

Those compounds of this invention having aspartic or glutamic acid moieties may be in free form or a salt form, e.g., acid addition or anionic salt. Such a compound may be converted into its salt or base form in an art-known manner, one from another. Preferred salts are trifluoroacetate, hydrochloride, sodium, potassium, or ammonium salts, although the scope of salts embraced herein is not limited thereto, the scope being extended to include all of the salts known to be used in the art of peptide chemistry.

Before further defining and/or illustrating the scope of the peptidase inhibitors embraced by formula I, it may be convenient to state some of the more basic concepts related to peptides. Each α-amino acid has a characteristic "R-group", the R-group being the side chain, or residue, attached to the α-carbon atom of the α-amino acid. For example, the R-group side chain for glycine is hydrogen, for alanine it is methyl, for valine it is isopropyl. (Thus, throughout this specification the R$_2$ moiety is the R-group for each indicated α-amino acid). For the specific R-groups—or side chains—of the α-amino acids reference to A. L. Lehninger's text on Biochemistry (see particularly Chapter 4) is helpful.

Those compounds of formula I wherein EIM or CGIM are a —C(O)C(O)R group can exist in a hydrated or unhydrated form. Hydrates of the triketo compounds having structure I' are much more chemically stable than are the unhydrated

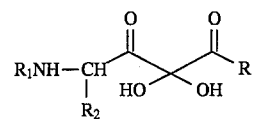

triketo compounds of formula I wherein EIM and/or CGIM is a —C(O)C(O)R group. For this reason, the hydrates are preferred and any reference in this specification and claims to a triketo compound should be taken to include reference to the corresponding hydrated form as context allows. Moreover, the compounds of this invention are expected to be in the hydrated form under normal physiological conditions.

The recognized abbreviations for the α-amino acids are set forth in Table I

TABLE I

| AMINO ACID | SYMBOL |
| --- | --- |
| Alanine | Ala |
| Arginine | Arg |
| Aspargine | Asn |
| Aspartic acid | Asp |
| Asn + Asp | Asx |
| Cysteine | Cys |
| Glutamine | Gln |
| Glutamic acid | Glu |
| Gln + Glu | Glx |
| Glycine | Gly |
| Histidine | His |
| Isoleucine | Ile |
| Leucine | Leu |
| Lysine | Lys |
| Methionine | Met |
| Phenylalanine | Phe |
| p-Guanidinophenylalanine | Phe(Gua) |
| Proline | Pro |
| Serine | Ser |
| Threonine | Thr |
| Tryptophan | Trp |
| Tyrosine | Tyr |
| Valine | Val |
| Norvaline | Nva |
| Norleucine | Nle |
| 1-Naphthylalanine | Nal(1) |
| 2-Indolinecarboxylic acid | Ind |
| Sarcosine | Sar |
| Cyclohexylalanine | Cha |
| beta-Alanine | bAla |
| beta-Valine | bVal |
| O-4'-Methyltyrosine | Tyr(Me) |
| 3-Pyrazolylalanine | Ala(3pyr) |
| 4-Pyrimidinylalanine | Ala(4pyr) |
| N$^6$-(2-carboxybenzoyl)lysine | Lys(2CBz) |
| Terephtholyl | tPht |
| N$^6$-acetyllysine | Lys(Ac) |

Applicants prefer those compounds of formula 1 wherein P$_1$ is norvaline or valine. Applicants also prefer those compounds of formula 1 wherein P$_1$ is norvaline or valine; P$_1$' is phenylalanine; P$_2$ is proline; P$_2$' is proline; P$_3$ is isoleucine, valine, or alanine; P$_3$' is alanine, valine, or is absent; P$_4$ is alanine or is absent; and wherein P$_4$' is alanine or is absent. Applicants prefer those compounds wherein L is a —C(O)-phenylene-C(O)— group, especially wherein the phenylene is a para-phenylene group. Applicants prefer those compounds of formula 1 wherein CGIM and EIM is a —CF$_3$ or —CF$_2$CF$_3$ group. Applicants especially prefer those compounds of formula 1 wherein -P$_4$-P$_3$-P$_2$-P$_1$- (SEQ ID NO: 2) is -Ala-Ala-Pro-Val- (SEQ ID NO: 3); -Lys(2CBz)-Pro-Val-; or -Val-Pro-Val- group. Applicants also especially prefer those compounds of formula 1 wherein -P$_4$'-P$_3$'-P$_2$'-P$_1$'- (SEQ ID NO: 4) is -Ala-Ala-Pro-Phe- (SEQ ID NO: 5); -Val-Pro-Phe-; or -Phe-. The most preferred compound of this invention includes

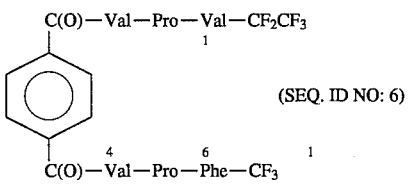

(SEQ. ID NO: 6)

The peptidase substrates of formula (I) are used for preventing connective tissue degradation such as cartilage degradation associated with neutrophil associated inflammatory disease and thus have an anti-inflammatory effect useful in the treatment of gout, rheumatoid arthritis and other inflammatory diseases, and to prevent elastin mediated tissue damage and thus can be used in the treatment of emphysema and adult respiratory disease syndrome (ARDS). In their end-use application the enzyme inhibitory properties of the compounds of (I) are readily ascertained by standard biochemical techniques well known in the art. Potential dose range for their end-use application will of course depend upon the nature and severity of the disease state as determined by the attending diagnostician with the range of 0.01 to 10 mg/kg body weight per day being useful for the aforementioned disease states with 0.1 mg to 10 mg/kg per day being preferred.

Having defined the scope of compounds embraced within the generic formula I, the manner in which such compounds may be prepared will herein below be described as illustrated. The preparation of the compounds of formula I may be achieved using standard chemical reactions analogously known to be useful for the preparation of a variety of known peptides. The preferred manner of preparing the compounds of this invention is to first prepare fragments corresponding to the elastase inhibiting peptide of formula 2 and the cathepsin G inhibiting peptide of formula 3,

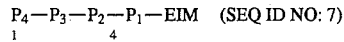

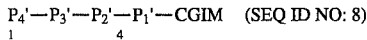

wherein $P_1$, $P_1'$, $P_2$, $P_2'$, $P_3$, $P_3'$, $P_4$, $P_4'$, EIM and CGIM are as defined for formula 1, and subsequently linking the two fragments with the "L" group. The elastase inhibiting peptide of form 2 and the cathepsin G inhibiting peptide of form 3 are, in general, prepared by first preparing the compounds of structure 4 and structure 5,

wherein $P_1$, $P_1'$ EIM and CGIM are as defined for formula 1, or protected or activated derivatives thereof, and subsequently using standard techniques known to those skilled in the field of peptide chemistry to add the desired amino acids. For this purpose, a handy reference text for these techniques is the 1985 "The Practice of Peptide Synthesis" by M. Bodanszky and A. Bodanszky, wherein the parameters and techniques affecting the selection, use and removal of protective groups for individual and groups of amino acids is detailed, and which also contains activation and coupling techniques and other special procedures. However, before the application of these peptide chemistry techniques may be applied, certain key intermediates containing the elastase inhibiting moiety (EIM) and the cathepsin G inhibiting moiety (CGIM) must first be prepared. The preparation of the key intermediates is described as follows.

Those compounds of formulae 2 or 3 may be prepared using standard chemical reactions analogously known in the art. More specifically the compounds of formulae 2 and 3 wherein EIM and CGIM are —$CF_2H$, —$CF_3$, —$CO_2R_3$, —$CONHR_3$, —$C(O)R$, —$CF_2CHR_3C(O)NHR$, H, alkyl, aryl, or aralkyl are known in art. Thus a description of the preparation of the compounds of formulae 2 or 3 wherein EIM or CGIM represents —$CF_2H$, —$CF_3$, —$CO_2R_3$, —$CONHR_3$, or —$C(O)R$ can be found in European Patent Application Number 195,212, published Sep. 24, 1986. A description of the preparation of the compounds of formulae 2 or 3 wherein EIM or CGIM represents —$CF_2CHR_3C(O)NHR$ are described in European Application Number 275,101, published Jul. 20, 1988. A description of the preparation of the compounds of formulae 2 and 3 wherein EIM and CGIM represents H, alkyl, aryl, or aralkyl are described in European Patent Application Number 363,284, published Apr. 11, 1990.

The preparation of the compounds of formula 2 wherein EIM or CGIM represents —$C(O)C(O)R$ is outlined in Scheme A wherein R, $P_1$, $P_2$, $P_3$, and $P_4$ are as previously defined. The compounds of formula 3 can be prepared in an analogous manner. Specifically, the compounds of formula 2 can be prepared by treatment of the appropriate ylide of formula 6 with (a) ozone and dimethyl sulfide or (b) singlet oxygen. The ozonylysis reaction can be conveniently performed by, for example, bubbling an excess of ozone through a cooled solution of the appropriate formula 6 ylide. Suitable solvents include any nonreactive solvent in which the formula 6 ylide is soluble, for example, alkyl esters of simple alkanoic acids such as ethyl acetate; the chlorinated hydrocarbons such as carbon tetrachloride, chloroform, 1,2-dichloroethane, 1,1,2,2-tetrachloroethane, and methylene chloride; the aromatic hydrocarbons such as benzene, toluene, and xylene; a chlorinated aromatic such as 1,2,4-trichlorobenzene and o-dichlorobenzene; an alcohol such as methanol, ethanol, and isopropanol; or an ethereal solvent such as diethyl ether, tetrahydrofuran (THF), and 1,4-dioxane. Methylene chloride is preferred.

Reaction Scheme A

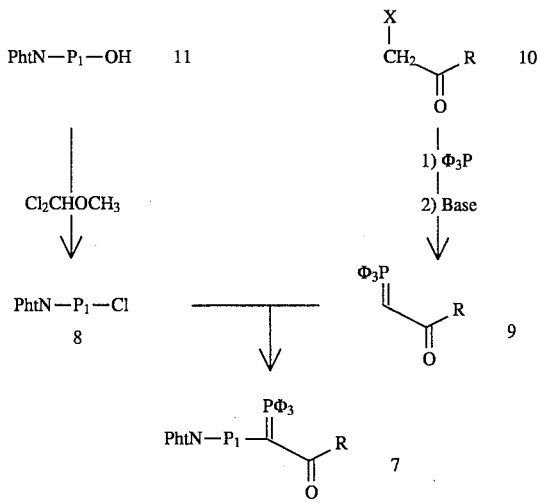

Reaction Scheme A (continued)

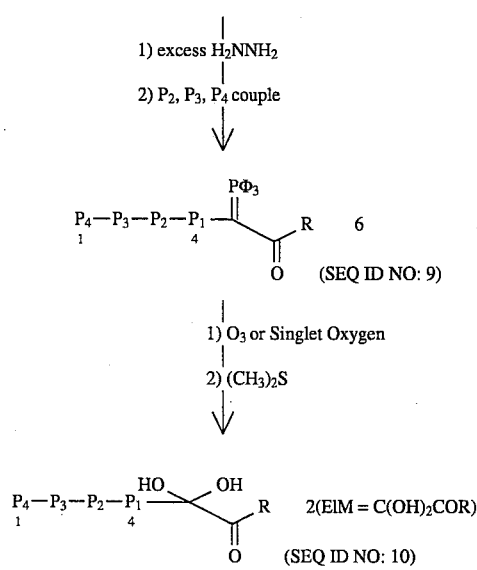

The temperature of the ozonolysis reaction mixture can be any temperature conducive to the reaction, typically from about −78° C. to about 0° C., preferably from about −78° C. to about −35° C., and most preferably about −70° C. The time of the reaction will vary depending on the ylide, the concentration of the reactants, the temperature and other factors. Conveniently, ozone is bubbled into the reaction mixture until the solution turns blue indicating an excess of oxone.

The ozonide is then treated with an excess of a reducing agent such as zinc metal or preferably dimethylsulfide. The desired formula 2 compound as the hydrate is isolated from the reaction mixture in any convenient manner, typically by solvent removal (via evaporation). Purification may be accomplished by, for example, flash chromatography.

Oxidations utilizing singlet oxygen are well known. More specifically, singlet oxygen oxidation of an ylide to produce a tricarbonyl ester has been reported by H. Wasserman et al., *J. Amer. Chem. Soc.* 11, 371 (1989).

Singlet oxygen can be generated by dye-sensitized excitation of oxygen. Suitable dyes include Rose Bengal, Eosin Y and methylene blue. Other sensitizers include dinaphthalenethiophene. Typically, Rose Bengal and Eosin Y are attached to a basic anion-exchange resin and methylene blue is attached to an acidic cation-exchange resin. Excitation is accomplished with a UV lamp such as a tungsten-iodine lamp. Suitable solvents are any solvents which promote and do not interfere with the desired reaction. Such solvents include the aromatic hydrocarbons such as benzene and toluene; hydrocarbons such as hexane; ethereal solvents such as diethyl ether, tetrahydrofuran (THF) 1,4-dioxane; chlorinated hydrocarbons such as dichloromethane and chloroform; carbon disulfide; and alcohols such as methanol, ethanol, propanol, isopropanol and t-butanol. Mixtures are operable. The temperature of the reaction mixture can be any suitable temperature from about −78° C. to about 30° C. typically from about −78° C. to about −50° C. The time of the reaction will vary depending on the reactant, the solvent, concentrations, and temperature and can be from about 1 min to about 2 hours. Purification and isolation can be by those methods described above for specification and isolation of product from the ozonolysis reaction mixture.

The formula 6 ylide is prepared from the appropriate N-protected ylide, preferably from the phthaloyl protected ylide of formula 7. The removal of the phthaloyl group can be readily achieved by methods generally known to those skilled in the art. For example, a solution of the phthaloyl ylide can be allowed to react with hydrazine hydrate, typically about a 20-fold excess of hydrazine hydrate, until the reaction is substantially complete. The solvent can be any of those described above for the ozonolysis reaction and preferably will be an alcohol solvent such as EtOH. The temperature of the reaction mixture can be from about 0° C. to about 60° C., conveniently at about room temperature, i.e., 25° C. The reaction time will vary depending on the specific reactant, the temperature, the solvent, and other factors known to influence reaction time. Conveniently, the progress of the reaction can be monitored by thin layer chromatography (TLC).

Subsequent to removal of the phthaloyl group, the $P_2$, $P_3$, and $P_4$ groups can be linked to the now free amino group. The $P_2$, $P_3$, and $P_4$ can be linked to the unprotected, free amino compound by well known peptide coupling techniques.

In coupling individual amino acids or peptides to the deprotected formula 7 compound, appropriate side chain protecting groups are employed. The selection and use of an appropriate protecting group for these side chain functionalities is within the ability of those skilled in the art and will depend upon the amino acid to be protected and the presence of other protected amino acid residues in the peptide. The selection of such a side chain protecting group is critical in that it must not be removed during the deprotection and coupling steps of the synthesis. For example, when Boc is used as the α-amino protecting group, the following side chain protecting groups are suitable: p-toluenesulfonyl (tosyl) moieties can be used to protect the amino side chains of amino acids such as Lys and Arg; p-methylbenzyl, acetamidomethyl, benzyl (Bzl), or t-butylsulfonyl moieties can be used to protect the sulfide containing side chains of amino acids such as cysteine, homocysteine, penicillamine and the like or derivatives thereof; benzyl (Bzl) or cyclohexyl ester moieties can be used to protect carboxylic acid side chains of amino acids such as Asp or Glu; a benzyl (Bzl) ether can be used to protect the hydroxy containing side chains of amino acids such as Ser and Thr; and a 2-bromocarbobenzoxy (Z(Br)) moiety can be used to protect the hydroxy containing side chains of amino acids such as Tyr. These side chain protecting groups are added and removed according to standard practices and procedures well known in the art. It is preferred to deprotect these side chain protecting groups with a solution of anisole in anhydrous hydrogen fluoride (1:10). Typically, deprotection of side chain protecting groups is performed after the peptide chain synthesis is complete but these groups can alternatively be removed at any other appropriate time. It is preferred to deprotect these side chains at the same time as the peptide is cleaved from the resin when solid phase synthetic methods are employed.

The phthaloyl ylide of formula 7 is prepared by reaction of the phthaloyl protected acid chloride of formula 8 with the phosphonium ylide of formula 9. This reaction is performed by adding a solution of the appropriate formula 9 ylide, preferably dropwise, to a solution of the formula 8 acid chloride. Suitable solvents include those listed above for the ozonolysis reaction and will preferably be an ethereal solvent such as THF. The reaction will require from about 30 minutes to about 12 hours, typically about 2 to 3 hours, depending on the acid chloride, the ylide, the solvent(s), and the temperature which can be from about 0° C. to about 60° C., conveniently at about room temperature, i.e., 25° C.

Isolation and purification is accomplished by filtering the reaction mixture to remove solid products and subsequently chromatographing the filtrate, for example, on silica gel eluting with a 50% mixture of ethyl acetate and hexane.

The formula 9 phosphorous ylide, Wittig reagent, is prepared from the corresponding formula 10 α-halocarboxylic acid derivative in the usual manner, that is, by reacting the α-halo ester with a tertiary phosphine such as triphenylphosphine to yield a phosphonium salt. When treated with a strong base such as an organolithium compound, for example, lithium diisopropylamide (LDA), sodium hydride, or sodium amide, the acidic proton is removed and the desired ylide is formed. Suitable solvents used in forming the Wittig reagent include any nonreactive solvent, for example, the aromatic hydrocarbons such as benzene or toluene, the chlorinated hydrocarbons such as carbon tetrachloride, chloroform, or methylene chloride, or the ethereal solvents such as diethyl ether or THF.

The reaction can conveniently be performed at from about 0° C. to about 60° C., typically at room temperature, that is about 25° C. The halo group of the α-halo ester is preferably a bromo group, but can be a chloro or iodo group or can be any good leaving group which forms a stable phosphonium salt such as a mesylate or tosylate group.

The acid chloride of formula 8 is prepared from the corresponding acid of formula 11 by, for example, reacting the acid with refluxing α,α-dichloromethyl methylether. After about 3 hours, the solution is allowed to cool and the product concentrated by solvent evaporation. The resulting crude acid chloride can be used directly without further purification in the reaction with the formula 9 phosphorous ylide.

The preparation of the compounds of formula 2 wherein EIM or CGIM represents —$CF_2CF_3$ is outlined in Scheme B wherein $R_1$ and $R_2$ are as previously defined, and Pg is an amino protecting group such as a carbamate, preferably a benzyloxycarbonyl (Cbz) group.

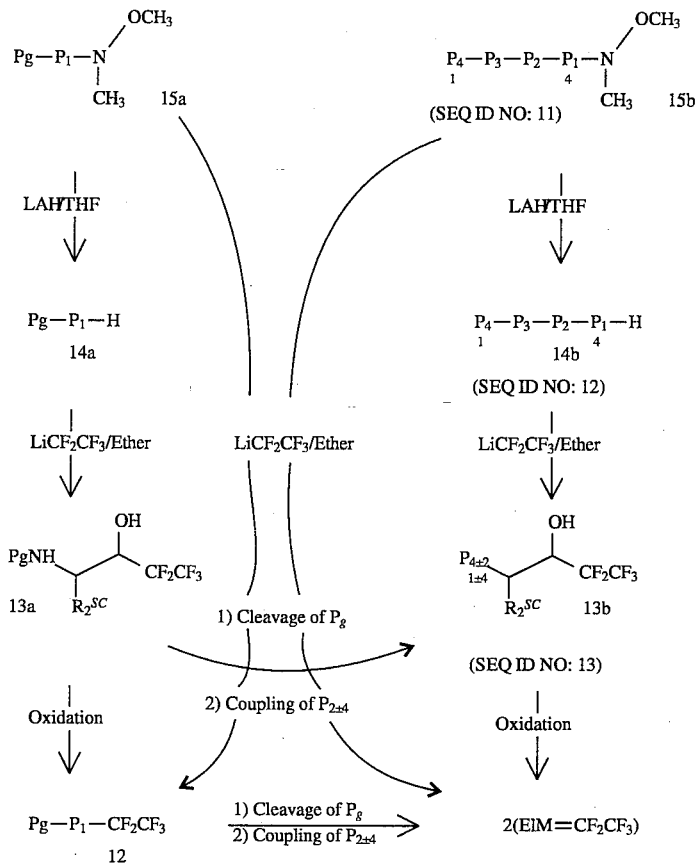

Reaction Scheme B

The compounds of formula 3 can be prepared in an analogous manner.

Specifically the compounds of this invention are prepared by reducing the N-methoxy-N-methyl amide of either formula 15a or 15b to produce the aldehydes of formulae 14a and 14b, respectively. Applicants prefer to use the compounds of formula 15a as the initial starting materials. The reduction can be performed in any way generally known and readily performed by those skilled in the art such as by use of lithium aluminum hydride (LAH). This reduction can be conveniently carried out by adding an excess of LAH to a cooled, typically about 0° C., solution of a formula 15a or 15b compound in a nonreactive solvent such as an ethereal solvent such as tetrahydrofuran (THF). After the reaction is substantially complete, typically after about 30 minutes, the reaction mixture is quenched by the addition of, for example, 10% potassium hydrogen sulfate and then water. The product can then be isolated by, for example, extraction of the aqueous mixture with a solvent such as ethyl acetate, drying and solvent removal. The crude product can be purified by, for example, column chromatography such as a silica gel column eluting with 55% ethyl acetate/hexane or recrystallization.

The formulae 14a and 14b aldehydes are then reacted with the pentafluoroethyl anion, such as the lithium salt of the pentafluoroethyl anion to give the alcohols of formulae 13a or 13b, respectively. This condensation can be conveniently preformed by those skilled in the art by a modified procedure as described by P. G. Gassman and Neil J. O'Reilly, J. Org. Chem. 1987, 52, 2481–2490. In this procedure, the perfluoroethyl anion is generated in situ by addition of methyllithium/lithium bromide complex to a solution of the aldehyde and pentafluoroethyl iodide in a nonreactive solvent such as diethyl ether. The cooled (−78°–0° C.) reaction mixture is allowed to stir for about one-half to about 1 hour or until the reaction is substantially complete and then the mixture is quenched by pouring into an excess of dilute hydrochloric acid. The product is isolated by, for example, extraction with diethyl ether and subsequent solvent removal. The crude product is purified by, for example, chromatography on silica gel.

The alcohols of formulae 13a or 13b are then oxidized to give the amino-protected pentafluoroethyl ketones of formula 12 or the desired product of formula 2, respectively. The oxidation may be effected via the well-known Swern oxidation procedure, or with a modified Jones oxidation using pyridinium dichromate, or a chromic anhydride-pyridinium complex, or with the Dess-Martin periodinane, 1,1,1-tris(acetyloxy)-1,1-dihydro-1,2-benzoiodoxol-3(1H)-one. Of course, if there are any protecting groups on the residues of the α-amino acid building blocks, such protecting groups may be removed after oxidation. The coupling procedures are effected according to standard procedures well known in the art.

In general the Swern oxidation is effected by reacting about 2 to 10 equivalents of dimethylsulfoxide (DMSO) with about 1 to 6 equivalents of trifluoroacetic anhydride [$(CF_3CO)_2O$] or oxalyl chloride [$(COCl)_2$], said reactants being dissolved in an inert solvent, e.g., methylene chloride ($CH_2Cl_2$), said reaction being under an inert atmosphere (e.g., nitrogen or equivalently functioning gas) under anhydrous conditions at temperatures of about −80° C. to −50° C. to form an in situ sulfonium adduct to which is added about 1 equivalent of an appropriate alcohol of formula 13a or 13b. Preferably, the alcohols are dissolved in an inert solvent, e.g., $CH_2Cl_2$ or minimum amounts of DMSO, and the reaction mixture is allowed to warm to about −50° C. (for about 10–20 minutes) and then the reaction is completed by adding about 3 to 10 equivalents of a tertiary amine, e.g., triethylamine, N-methylmorpholine, etc.

In general, the modified Jones oxidation procedure may conveniently be effected by reacting an alcohol of formula 13a or 13b with pyridinium dichromate by contacting the reactants together in a water-trapping molecular sieve powder, (e.g., a powdered 3 Angstrom molecular sieve), wherein said contact is in the presence of glacial acetic acid at about 0° C. to 50° C., preferably at room temperature followed by isolation and then optionally removing amine protecting groups.

Alternatively, 1 to 5 equivalents of a chromic anhydride-pyridine complex (i.e., a Sarett reagent prepared in situ (see Fieser and Fieser "Reagents for Organic Synthesis" Vol. 1, pp. 145 and Sarett, et al., J.A.C.S. 25, 422, (1953)) said complex being prepared in situ in an inert solvent (e.g., $CH_2Cl_2$) in an inert atmosphere under anhydrous conditions at 0° C. to 50° C. to which complex is added 1 equivalent of an alcohol of formula 13a or 13b allowing the reactants to interact for about 1 to 15 hours, followed by isolation and optionally removing amine protecting groups.

Another alternative process for converting an alcohol of formula 13a or 13b to the desired ketone of formula 1 or 5 is an oxidation reaction which employs Dess-Martin periodinane (see Dess and Martin, J. Org. Chem., 48, 4155, (1983)). This oxidation is effected by contacting about 1 equivalent of the appropriate alcohol of formula 13a or 13b with 1 to 5 equivalents of periodinane (preferably 1.5 equivalents), said reagent being in suspension in an inert solvent (e.g., methylene chloride) under an inert atmosphere (preferably nitrogen) under anhydrous conditions at 0° C. to 50° C. (preferably room temperature) and allowing the reactants to interact for about 1 to 48 hours. Optional deprotection of the amine protecting groups may be effected as desired after the ketones have been isolated.

In one mode of preparing the compounds of this invention the formula compounds are prepared by first converting the amino-protected, perfluoroethyl alcohol of formula 13a to the corresponding compound of formula 13b, prior to final oxidation. The amino-protected, perfluoroethyl alcohol of formula 13a is first deprotected, if desired, and then any amino acids or peptide chain represented by $P_4$-$P_3$-$P_2$- can be added using standard α-amino acid or peptide coupling procedures. Where the $P_4$-$P_3$-$P_2$- group is made up of more than one amino acid, either the entire peptide chain can be added to the deprotected formula 13a compound or the amino acids can be coupled to the deprotected formula 13a compound sequentially. Alternatively, a combination of these two coupling methods can be used. In a like manner, the compounds of formula 12 can be converted to the desired formula 2 compounds.

In coupling individual amino acids or peptides to the deprotected formula 13a or formula 12 compounds, appropriate side chain protecting groups are employed. The selection and use of an appropriate protecting group for these side chain functionalities is within the ability of those skilled in the art and will depend upon the amino acid to be protected and the presence of other protected amino acid residues in the peptide. The selection of such a side chain protecting group is critical in that it must not be removed during the deprotection and coupling steps of the synthesis. For example, when Boc is used as the α-amino protecting group, the following side chain protecting groups are suitable: p-toluenesulfonyl (tosyl) moieties can be used to protect the amine side chains of amino acids such as Lys and Arg; p-methylbenzyl, acetamidomethyl, benzyl (Bzl), or t-butylsulfonyl moieties can be used to protect the sulfide containing side chains of amino acids such as cysteine, homocysteine, penicillamine and the like or derivatives thereof; benzyl (Bzl) or cyclohexyl ester moieties can be used to protect carboxylic acid side chains of amino acids such as Asp, Glu; a benzyl (Bzl) ether can be used to protect the hydroxy containing side chains of amino acids such as Ser and Thr; and a 2-bromocarbobenzoxy (2Br-Z) moiety can be used to protect the hydroxy containing side chains of amino acids such as Tyr. These side chain protecting groups are added and removed according to standard practices and procedures well known in the art. It is preferred to deprotect these side chain protecting groups with a solution of anisole in anhydrous hydrogen fluoride (1:10). Typically, deprotection of side chain protecting groups is performed after the peptide chain synthesis is complete but these groups can alternatively be removed at any other appropriate time. It is preferred to deprotect these side chains at the same time as the peptide is cleaved from the resin when solid phase synthetic methods are employed.

In the preferred mode of preparing the compounds of this invention, the compounds of formulae 15a and 15b can be converted directly to the compounds of formulae 12 or 2, respectively, by condensation of the N-methoxy-N-methyl amide with the lithium salt of the perfluoroethyl anion in the same manner in which the compounds of formulae 15a and 15b are converted to the compounds of formulae 14a and 14b, respectively.

The compounds are then isolated and purified by standard techniques. The desired amino acids, derivatives and isomers thereof can be obtained commercially or can be synthesized according to standard practices and procedures well known in the art.

The N-methoxy-N-methyl amides of formulae 15a and 15b are prepared from the corresponding α-amino acids of formulae 16a and 16b, wherein $R_1$ and $R_2$ are as defined for formula 1 and wherein Pg is an amino protecting group such as carbamate, preferably a benzyloxycarbonyl (Cbz) group, respectively, in the usual manner. (See, for example, J. A. Fehrentz and B. Castro, *Synthesis*, 676–78 (1983).

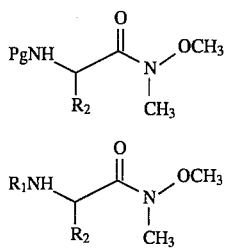

Isobutylchloroformate is added to a cooled (i.e. −60° C. to about 0° C.) mixture of N-methylmorpholine or another sterically hindered, non-nucleophilic tertiary amine and an α-amino acid compound in a nonreactive solvent such as methylene chloride. After about 5 minutes to about 1 hour, typically about 15–20 minutes, N,O-dimethylhydroxylamine HCl is added and the mixture allowed to stir for from about 30 minutes up to about 6 hours and then the reaction mixture is allowed to warm to room temperature. When the reaction is substantially complete, typically after about 1 to about 10 hours, the mixture is poured into water and the aqueous phase is extracted with, for example, ethyl acetate. The desired compound is then isolated by solvent evaporation and crude purification can be accomplished by, for example, flash chromatography on silica gel eluting with ethyl acetate/hexane. Purification can be accomplished by, for example, flash chromatography on silica gel eluting with methylene chloride.

The compounds of formula (1) wherein $L_1$ and $L_2$ are both represented by carbonyl groups, $L_1$ and $L_2$ are both represented by sulfonyl groups or $L_2$ is represented by a carbonyl group and $L_1$ is represented by a sulfonyl group can be prepared by techniques and procedures well known an appreciated by one of ordinary skill in the art. A general synthetic scheme for preparing these compounds of formula (1) is set forth in Scheme C. In Scheme C, all substituents unless otherwise indicated are as previously defined.

Scheme C

COUPLING

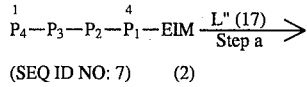

(SEQ ID NO: 7)   (2)

-continued
Scheme C

COUPLING

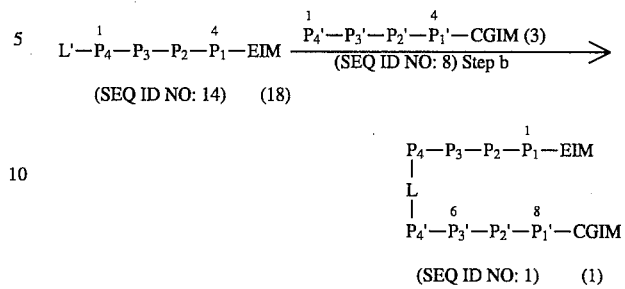

L" = an appropriate di-functionalized derivative of L
L' = an appropriate mono-functionalized derivative of L Scheme C provides a general synthetic procedure for preparing the compounds of formula (1) wherein $L_1$ and $L_2$ are both represented by carbonyl groups, $L_1$ and $L_2$ are both represented by sulfonyl groups or $L_2$ is represented by a carbonyl group and $L_1$ is represented by a sulfonyl group. In step a, the appropriate elastase inhibiting peptide fragment of formula (2) is coupled with the appropriate derivative of L as described by structure (17) to give the corresponding L-elastase inhibiting peptide fragment of structure (18) by techniques well known in the art.

When the compound of formula (1) is one wherein $L_1$ and $L_2$ are both represented by carbonyl groups, an appropriate derivative of L as described by structure (17) is one wherein the $L_2$ carbonyl group is represented by a t-butyloxycarbonyl protected carboxylic acid and the $L_1$ carbonyl group is represented by an unprotected carboxylic acid.

When the compound of formula (1) is one wherein $L_1$ and $L_2$ are both represented by sulfonyl groups, an appropriate derivative of L as described by structure (17) is one wherein the $L_1$ sulfonyl group is represented by a sulfonyl chloride group and the $L_2$ sulfonyl group is represented by an unprotected sulfonic acid.

When the compound of formula (1) is one wherein $L_2$ is represented by a carbonyl group and $L_1$ is represented by a sulfonyl group, an appropriate derivative of L as described by structure (17) is one wherein the $L_2$ carbonyl group is represented by a t-butyloxycarbonyl protected carboxylic acid and the $L_1$ sulfonyl group is represented by a sulfonyl chloride group.

In step b, the appropriate L-elastase inhibiting peptide fragment of structure (18) is coupled with the appropriate cathepsin G inhibiting peptide fragment of formula (3) to give the corresponding compound of formula (1) by techniques well known in the art.

When the appropriate L-elastase inhibiting peptide fragment of structure (18) is one wherein the $L_2$ carbonyl group is represented by a t-butyloxycarbonyl protected carboxylic acid, the t-butyloxycarbonyl protected carboxylic acid must first be hydrolyzed by techniques well known in the art prior to the coupling reaction in step b.

Starting materials for use in Scheme C are readily available to one of ordinary skill in the art.

The compounds of formula (1) wherein $L_1$ is represented by a carbonyl group and $L_2$ is represented by a sulfonyl group can be prepared by techniques and procedures well known an appreciated by one of ordinary skill in the art. A general synthetic scheme for preparing these compounds of formula (1) is set forth in Scheme D. In Scheme D, all substituents unless otherwise indicated are as previously defined.

Scheme D

COUPLING

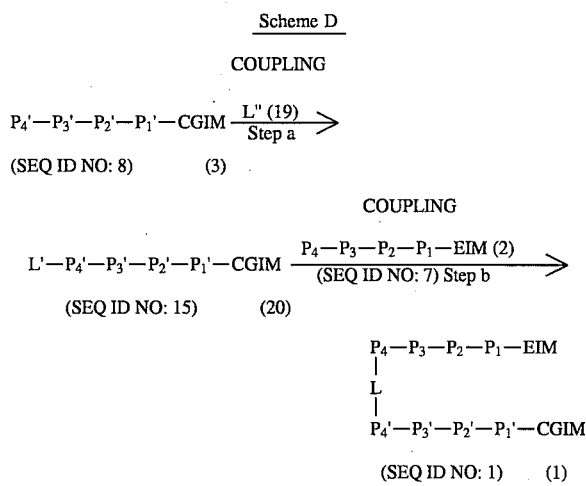

L" = an appropriate di-functionalized derivative of L
L' = an appropriate mono-functionalized derivative of L Scheme D provides a general synthetic procedure for preparing the compounds of formula (1) wherein $L_1$ is represented by a carbonyl group and $L_2$ is represented by a sulfonyl group.

In step a, the appropriate cathepsin G inhibiting peptide fragment of formula (3) is coupled with the appropriate derivative of L as described by structure (19) to give the corresponding cathepsin G inhibiting peptide fragment of structure (20) by techniques well known in the art.

An appropriate derivative of L as described by structure (19) is one wherein the $L_1$ carbonyl group is represented by a t-butyloxycarbonyl protected carboxylic acid and the $L_2$ carbonyl group is represented by a sulfonyl chloride group.

In step b, the appropriate cathepsin G inhibiting peptide inhibiting peptide fragment of structure (20) is coupled with the appropriate elastase inhibiting peptide fragment of formula (2) to give the corresponding compound of formula (1) by techniques well known in the art.

The t-butyloxycarbonyl protected carboxylic acid functionality on $L_1$ of the appropriate cathepsin G inhibiting peptide inhibiting peptide fragment of structure (20) must first be hydrolyzed by techniques well known in the art prior to the coupling reaction in step b.

Starting materials for use in Scheme D are readily available to one of ordinary skill in the art.

The following specific examples are given to illustrate the preparation of this invention although the scope of compounds is not meant to be limiting to the scope of compounds embraced by formula I.

EXAMPLE 1

[CF$_3$]Phe-Pro-Val-C(O)-phenylene-C(O)-Val-Pro-Val[CF$_2$CF$_3$]-SEQ ID NO: 6

Preparation of Boc-Val[CF$_2$CF$_3$]

Dissolve Boc-Val dimethylhydroxyamide (1.0 g, 3.8 mmol) in ethyl ether (50 mL) and cool to −78° C. Add pentafluoroethyl iodide (3 g, 12.2 mmol) followed by methyllithium.lithium bromide complex (6 mL of a 1.5M solution). Repeat the addition of pentafluoroethyl iodide (3 g, 12.2 mmol) followed by methyllithium.lithium bromide complex (6 mL of a 1.5M solution) three times. Stir for 15 minutes at −78° C. then allow to warm to room temperature. Pour into water and separate the organic phase. Extract the aqueous phase with ethyl ether (3×150 mL), combine the organic phases and dry (Na$_2$SO$_4$). Evaporate the solvent in vacuo and purify by silica gel chromatography (10% ethyl acetate/hexane) to give the title compound.

Preparation of Val[CF$_2$CF$_3$].hydrochloride

Dissolve Boc-Val[CF$_2$CF$_3$] (350 mg, 1.1 mmol) in ethyl acetate (50 mL) and cool to 0° C. Treat with hydrogen chloride gas for 5 minutes and stir for 30 minutes. Remove the solvent in vacuo to give the title compound.

Preparation of Boc-Val-Pro-Val[CF$_2$CF$_3$]

Dissolve Boc-Val-Pro (314 mg, 1.0 mmol) in methylene chloride (4 mL) and add N-methylmorpholine (252 mg, 2.5 mmol). Cool to −22° C. and add isobutylchloroformate (136 mg, 1.0 mmol). Stir for 20 minutes and add to Val[CF$_2$CF$_3$].hydrochloride (1.1 mmol). Stir for 1 hour at −22° C., allow to warm to room temperature and stir for 3 hours. Purify by silica gel chromatography (40% ethyl acetate/hexane) to give the title compound (405 mg).

Preparation of Val-Pro-Val[CF$_2$CF$_3$].hydrochloride

Dissolve Boc-Val-Pro-Val[CF$_2$CF$_3$] (385 mg, 0.74 mmol) in ethyl acetate (50 mL) and cool to 0° C. Treat with hydrogen chloride gas for 5 minutes and stir for 30 minutes. Evaporate the solvent in vacuo to give the title compound (334 mg).

Preparation of Boc-Val-Pro-Phe[OH][CF$_3$]

Mix 2-phenyl-66 $^2$-oxazoline-4-phenylmethyl-5-one (Synthesis, #3, 191–3, (1982)) (300 g) and trifluoroacetic anhydride (700 g). Heat at reflux for 3 hours then stir overnight at room temperature. Evaporate the solvent in vacuo and add oxalic acid (400 g). Stir and add additional oxalic acid (50 g). Heat until evolution of CO$_2$ ceases and a solid forms. Cool to room temperature and dissolve in a 1:3 mixture of water/ethyl acetate (12 L). Separate the organic phase, wash until basic with saturated sodium hydrogen carbonate then with water. Dry (MgSO$_4$), filter and concentrate by boiling to a volume of 2.5 L. Cool to room temperature and add hexane (1 L). Filter the precipitated solid and air dry to give 1,1,1-trifluoro-2-one-3-benzoylamino-4-phenylbutane (187.6 g).

Dissolve 1,1,1-trifluoro-2-one-3-benzoylamino-4-phenylbutane (187.6 g) in ethanol (1 L) and cool in an ice bath. Add sodium borohydride (11 g) in portions over 15 minutes. Remove the ice bath and stir at room temperature to 1.5 hours. Replace the ice bath and carefully treat with 10% hydrochloric acid (250 mL). Add ethyl acetate (4 L) to dissolve and then add water (500 mL). Separate the organic phase, wash with brine (4×300 mL) and dry (MgSO$_4$). Filter and evaporate the solvent in vacuo. Add hexane and filter to give 1,1,1-trifluoro-3-benzoylamino-4-phenyl-2-butanol as a white solid (145.2 g).

Mix 1,1,1-trifluoro-3-benzoylamino-4-phenyl-2-butanol (145.2 g), concentrated hydrochloric acid (1.4 L), water (700 mL) and ethanol (1 L). Heat to reflux for 24 hours then add additional concentrated hydrochloric acid (400 mL) and ethanol (1.2 L). Stir an additional 24 hours. Evaporate the ethanol in vacuo and filter. Cool the filtrate to room temperature and treat with sodium hydrogen carbonate and then with 50% sodium hydroxide while cooling in an ice bath. When pH 10 is obtained, filter off the solid to give [CF$_3$][OH]-phe (58.2 g).

Dissolve Boc-Val-Pro (3.3 g, 10.5 mmol) in methylene chloride (25 mL) and add N-methylmorpholine (2.12 g, 21 mmol). Cool to −22° C. and add isobutylchloroformate (1.43 g, 10.5 mmol). Stir at −22° C. for 25 minutes then add [CF$_3$][OH]-phe (2.5 g, 11.5 mmol). Stir at −22° C. for 3 hours, allow to warm to room temperature and stir overnight. Pour into water (100 mL) and extract into ethyl ether (3×150 mL). Wash the combined organic phases with dilute hydrochloride acid then saturated sodium hydrogen carbonate. Dry ($Na_2SO_4$) and evaporate the solvent in vacuo. Purify by silica gel chromatography (40% ethyl acetate/hexane) to give the title compound (5.27 g).

Preparation of Boc-Val-Pro-Phe[$CF_3$]

Dissolve Boc-Val-Pro-Phe[OH][$CF_3$] (0.79 g, 1.54 mmol) in methylene chloride (25 mL) and add Dess-Martin reagent (2.5 g). Stir at room temperature overnight then pour into 50 mL of water containing sodium hydrogen carbonate (1.0 g) and sodium bisulfite (1.7 g). Extract with ethyl ether (3×100 mL) and dry ($Na_2SO_4$). Evaporate the solvent in vacuo and purify by silica gel chromatography (40% ethyl acetate/hexane) to give the title compound (755 mg).

Preparation of Val-Pro-Phe[$CF_3$].hydrochloride

Dissolve Boc-Val-Pro-Phe[$CF_3$] in ethyl acetate (100 mL) and cool to 0° C. Treat with hydrogen chloride gas for 5 minutes and stir at 0° C. for 30 minutes. Evaporate the solvent in vacuo to give the title compound (840 mg).

Preparation of BOC-phenylene-C(O)-Val-Pro-Phe[$CF_3$]

Dissolve Boc-phenylene-C(O)OH (370 mg, 1.67 mmol) in methylene chloride (4 mL) and N-methylmorpholine (0.18 mL, 1.67 mmol). Cool to −20° C. and add isobutylchloroformate (0.227 g, 1.76 mmol) and stir for 45 minutes. Ada methylene chloride (2 mL) and add N-methylmorpholine (0.18 mL) and Val-Pro-Phe[CF3].hydrochloride 0.75 g, 1.67 mmol). Stir at −20° C. for 2 hours, allow to warm to room temperature and stir for an additional 3 hours. Pour into a mixture of methylene chloride (10 mL) and water (20 mL). Separate the organic phase and extract the aqueous phase with methylene chloride (2×20 mL). Combine the organic phases and dry ($Na_2SO_4$). Evaporate the solvent in vacuo and purify by silica gel chromatography to give the title compound (575 mg).

Preparation of $H_2OC$-phenylene-C(O)-Val-Pro-Phe[$CF_3$] .hydrochloride

Dissolve Boc-phenylene-C(O)-Val-Pro-Phe[$CF_3$] (250 mg) in ethyl acetate (50 mL) and cool to 0° C. Treat with hydrogen chloride gas for 5 minutes and stir at 0° C. for 1 hour. Evaporate the solvent in vacuo to give the title compound (232 mg).

Preparation of [$CF_3$]Phe-Pro-Val-C(O)-phenylene-C(O)-Val-Pro-Val[$CF_2CF_3$]-SEQ ID NO: 6

Dissolve $H_2OC$-phenylene-C(O)-Val-Pro-Phe[$CF_3$].hydrochloride (230 mg, 0.41 mmol) in methylene chloride (3 mL) and add N-methylmorpholine (41.4 mg, 0.41 mmol). Cool to −20° C. and add isobutylchloroformate (55.7 mg, 0.41 mmol). Stir for 45 minutes at −20° C. and add Val-Pro-Val[$CF_2CF_3$].hydrochloride (185 mg, 0.41 mmol). Stir at −22° C. for 3 hours, allow to warm to room temperature and stir for an additional 3 hours. Pour into water and extract into methylene chloride (3×25 mL). Combine the organic phases and dry ($Na_2SO_4$). Evaporate the solvent in vacuo and purify by silica gel chromatography (ethyl acetate then methanol) to give the title compound (190 mg).

EXAMPLE 2

[$CF_3$]Phe-C(O)-phenylene-C(O)-Val-Pro-Val[$CF_2C_3$]-SEQ ID NO: 16

Preparation of Boc-phenylene-C(O)-Phe[OH][$CF_3$]

Dissolve Boc-phenylene-C(O)OH (0.615 g, 2.8 mmol) in methylene chloride (6 mL) and add N-methylmorpholine (0.6 g). Cool to −22° C. and add isobutylchloroformate (0.4 mL, 3.08 mmol). Stir at −22° C. for 25 minutes and add a solution of Phe[OH][$CF_3$] (0.64 g, 2.9 mmol) in methylene chloride (2 mL) and N-methylmorpholine (0.3 g). Stir at −22° C. for 1 hour, allow to warm to room temperature and stir an additional 2 hours. Pour the mixture into water (100 mL) and extract into ethyl ether (100 mL then 50 mL). Combine the organic phases and dry ($Na_2SO_4$). Evaporate the solvent in vacuo and purify by silica gel chromatography (40% ethyl acetate/hexane) to give the title compound (840 mg).

Preparation of Boc-phenylene-C(O)-Phe[$CF_3$]

Dissolve Boc-phenylene-C(O)-Phe[OH][$CF_3$] (0.6 g) in methylene chloride (25 mL) and add Dess-Martin reagent (1.8 g). Stir for 48 hour and pour into a mixture of sodium hydrogen carbonate (0.8 g) and sodium bisulfite (1.41 g) in water (25 mL) and ethyl ether (100 mL). Separate the organic phase and extract the aqueous phase with ethyl ether (50 mL). Combine the organic phases and dry ($MgSO_4$). Evaporate the solvent in vacuo and purify by silica gel chromatography (25% ethyl acetate/hexane) to give the title compound (430 mg).

Preparation of $H_2OC$-phenylene-C(O)-Phe[$CF_3$]

Dissolve Boc-phenylene-C(O)-Phe[$CF_3$] (216 mg, 0.51 mmol) in ethyl acetate (50 mL) and cool to 0° C. Treat with hydrogen chloride gas for 5 minutes and stir for 3 hours. Evaporate the solvent in vacuo to give the title compound 197 mg).

Preparation of [$CF_3$]Phe-C(O)-phenylene-C(O)-Val-Pro-Val[$CF_2CF_3$]-SEQ ID NO: 16

Suspend $H_2OC$-phenylene-C(O)-Phe[$CF_3$] (175 mg) in methylene chloride (2 mL) and add N-methylmorpholine (100 μL). Cool to −22° C. and add isobutylchloroformate (65 μL). Stir at −22° C. for 25 minutes and add a solution of Val-Pro-Val[$CF_2CF_3$] (240 mg) in methylene chloride (2 mL) and N-methylmorpholine (60 μL). Stir at −22 ° C. for 30 minutes, allow to warm to room temperature and stir for an additional 1.5 hours. Evaporate the solvent in vacuo to approximately 1 mL volume and purify by silica gel chromatography (50% ethyl acetate/hexane) to give the title compound (110 mg).

EXAMPLE 3

[$CF_3$]Phe-Pro-Val-C(O)-Val-Pro-Val[$CF_2CF_3$]-SEQ ID NO: 17

Partition Val-Pro-Val[$CF_2CF_3$].hydrochloride (200 mg) between ethyl acetate (10 mL) and saturated sodium hydrogen carbonate (20 mL). Separate the organic phase and extract the aqueous phase with ethyl acetate (3×20 mL). Combine the organic phases, dry ($MgSO_4$) and evaporate the solvent in vacuo to give Val-Pro-Val[$CF_2CF_3$].

Partition Val-Pro-Phe[$CF_3$].hydrochloride (200 mg) between ethyl acetate (10 mL) and saturated sodium hydrogen carbonate (20 mL). Separate the organic phase and extract the aqueous phase with ethyl acetate (3×20 mL). Combine the organic phases, dry ($MgSO_4$) and evaporate the solvent in vacuo to give Val-Pro-Phe[$CF_3$].

Dissolve phosgene (545 mg, 5.51 mmol) in benzene (3.5 mL) and slowly add a solution of Val-Pro-Val[$CF_2CF_3$] (568 mg, 1.37 mmol) in benzene (1 mL). Stir at 60°–75° C. for several hours then reflux vigorously for 2 hours. Remove approximately ½ the benzene by distillation and cool the remaining solution in an ice bath. Add a solution of Val-Pro-Phe[$CF_3$] (500 mg, 1.37 mmol) in ethyl ether (2 mL) and stir at room temperature for several hours. Evaporate the solvent in vacuo and purify by chromatography to give the title compound.

EXAMPLE 4

[CF$_3$]Phe-Pro-Val-CH$_2$-CH$_2$-Val-Pro-Val[CF$_2$CF$_3$]-SEQ ID NO: 18

Dissolve Val-Pro-Val[CF$_2$CF$_3$] (568 mg, 1.37 mmol) and Val-Pro-Phe[CF$_3$] (500 mg, 1.37 mmol) in methanol (20 mL) and add glyoxal (200 mg of a 40% solution in water, 1.37 mmol), sodium cyanoborohydride (86 mg, 1.37 mmol) and 1 drop of 1% bromocresol green in ethanol. Maintain the pH of the reaction with 1N hydrochloric acid in methanol until the indicator no longer changes. Evaporate the solvent in vacuo and partition the residue between 1N sodium hydroxide (5 mL) and ethyl acetate (10 mL). Separate the organic phase, dry (MgSO$_4$) and evaporate the solvent in vacuo. Purify by chromatography to give the title compound.

---

What is claimed is:

1. A compound of the formula

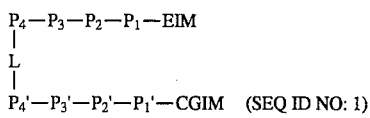

wherein $P_1$ is Val or Nva;

$P_1'$ is Phe;

$P_2$ is Pro;

$P_2'$ is Pro or is absent;

$P_3$ is Lys, Ala, Ile or Val;

$P_3'$ is Ala, Val or is absent;

$P_4$ is Ala or is absent;

$P_4'$ is Ala or is absent;

L is a —C(O)-phenylene-C(O)— group;

EIM and CGIM are each independently selected from the group consisting of —$CF_2CF_3$, —$CF_3$, —$CF_2H$, —$CO_2R_3$, —$CONHR_3$, —H, or —C(O)R, wherein $R_3$ is H, alkyl, phenyl, benzyl, R is OH or alkoxy or a pharmaceutically acceptable salt thereof.

2. A compound of claim 1 wherein CGIM and EIM are each independently either a —$CF_3$ or —$CF_2CF_3$ group.

3. A compound of claim 1 wherein -$P_4$-$P_3$-$P_2$-$P_1$ (SEQ ID NO: 2) is a-Ala-Ala-Pro-Val- (SEQ ID NO: 3); -Lys(2CBz)-Pro-Val-; or -Val-Pro-Val- group.

4. A compound of claim 2 wherein -$P_4$-$P_3$-$P_2$-$P_1$ (SEQ ID NO: 2) is a -Ala-Ala-Pro-Val- (SEQ ID NO: 3); -Lys(2CBz)-Pro-Val-; or -Val-Pro-Val- group.

5. A compound of claim 1 wherein -$P_4'$-$P_3'$-$P_2'$-$P_1'$ (SEQ ID NO: 4) is a -Ala-Ala-Pro-Phe (SEQ ID NO: 5); -Val-Pro-Phe-; or -Phe- group.

6. A compound of claim 2 wherein -$P_4'$-$P_3'$-$P_2'$-$P_1'$ (SEQ ID NO: 4) is a -Ala-Ala-Pro-Phe (SEQ ID NO: 5); -Val-Pro-Phe-; or -Phe- group.

7. A compound of claim 1 which is

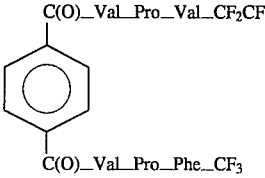

SEQ ID NO: 6)

8. A method of treating gout or rheumatoid arthritis in a patient in need thereof which comprises administering to the patient an anti-inflammatory effective amount of a compound of claim 1.

9. A method of treating neutrophil associated inflammatory disease in a patient in need thereof which comprises administering to the patient a connective tissue degradation inhibiting amount of a compound of claim 1.

10. A method for treating conditions associated with connective tissue degradation in a patient in need thereof which comprises administering to the patient a connective tissue degradation inhibiting amount of a compound of claim 1.

* * * * *

UNITED STATES PATENT AND TRADEMARK OFFICE
CERTIFICATE OF CORRECTION

PATENT NO. : 5,510,333

DATED : April 23, 1996

INVENTOR(S) : Angelastro et al

It is certified that error appears in the above-indentified patent and that said Letters Patent is hereby corrected as shown below:

Column 13, Line 55 Patent reads: "well known an" and should read --well known and--.

Column 14, Line 62 Patent reads: "known an appreciated" and should read --known and appreciated--.

Column 16, Line 25 Patent reads: "2-phenyl-66 $^{2}$" and should read --2-phenyl-$\Delta^2$--.

Column 17, Line 58 Patent reads: "[CF$_2$C$_3$]" and should read --[CF$_2$CF$_3$]--.

Column 18, Line 11 Patent reads: "48 hour" and should read --48 hours--.

Signed and Sealed this

Tenth Day of June, 1997

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Xaa Xaa Xaa Xaa Xaa Xaa Xaa Xaa
1               5

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Xaa Xaa Xaa Xaa
1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Ala Ala Pro Val
1

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Xaa Xaa Xaa Xaa
1

( 2 ) INFORMATION FOR SEQ ID NO:5:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:5:

Ala Ala Pro Phe
1

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="Xaa is a valine analog
            having a - CF2CF3 group replacing the hydroxy of
            the terminal carboxy."

( i x ) FEATURE:
        ( A ) NAME/KEY: Modified-site
        ( B ) LOCATION: 3
        ( D ) OTHER INFORMATION: /note="Xaa is a valine analog
            having a -L1- Ph-L2- group replacing one of the
            hydrogens on the amino terminus wherein L1 and L2"

( i x ) FEATURE:
        ( A ) NAME/KEY: Modified-site
        ( B ) LOCATION: 3
        ( D ) OTHER INFORMATION: /note="(cont) are each a carbonyl
            wherein L1 is bound to the peptide fragment
            containing the modified sites at locations 1-2"

( i x ) FEATURE:
        ( A ) NAME/KEY: Modified-site
        ( B ) LOCATION: 3
        ( D ) OTHER INFORMATION: /note="(cont)and L2 is bound to
            the peptide fragment containing the modified sites
            at locations 4-6 and Ph is a p-phenylene group."

( i x ) FEATURE:
        ( A ) NAME/KEY: Modified-site
        ( B ) LOCATION: 6
        ( D ) OTHER INFORMATION: /note="Xaa is a phenylalanine
            analog having a -CF3 group replacing the hydroxy
            of the terminal carboxy"

( x i ) SEQUENCE DESCRIPTION: SEQ ID NO:6:

Xaa Pro Xaa Val Pro Xaa
1               5

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

Xaa Xaa Xaa Xaa
1

( 2 ) INFORMATION FOR SEQ ID NO:8:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:8:

Xaa Xaa Xaa Xaa
1

( 2 ) INFORMATION FOR SEQ ID NO:9:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Xaa Xaa Xaa Xaa
1

( 2 ) INFORMATION FOR SEQ ID NO:10:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

Xaa Xaa Xaa Xaa
1

( 2 ) INFORMATION FOR SEQ ID NO:11:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

Xaa Xaa Xaa Xaa
1

( 2 ) INFORMATION FOR SEQ ID NO:12:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

Xaa Xaa Xaa Xaa
1

( 2 ) INFORMATION FOR SEQ ID NO:13:

( i ) SEQUENCE CHARACTERISTICS:
        ( A ) LENGTH: 4 amino acids
        ( B ) TYPE: amino acid
        ( D ) TOPOLOGY: linear (ii) MOLECULE TYPE: peptide (xi) SEQUENCE DESCRIPTION: SEQ ID NO:13:

Xaa Xaa Xaa Xaa
1

(2) INFORMATION FOR SEQ ID NO:14:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:14:

Xaa Xaa Xaa Xaa
1

(2) INFORMATION FOR SEQ ID NO:15:

(i) SEQUENCE CHARACTERISTICS:
(A) LENGTH: 4 amino acids
(B) TYPE: amino acid
(D) TOPOLOGY: linear (ii) MOLECULE TYPE: peptide (xi) SEQUENCE DESCRIPTION: SEQ ID NO:15:

Xaa Xaa Xaa Xaa
1

(2) INFORMATION FOR SEQ ID NO:16:

(i) SEQUENCE CHARACTERISTICS:
(A) LENGTH: 4 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="Xaa is a valine analog
having a - CF2CF3 group replacing the hydroxy of
the terminal carboxy."

(ix) FEATURE:
(A) NAME/KEY: Modified-site
(B) LOCATION: 3
(D) OTHER INFORMATION: /note="Xaa is a valine analog
having a -L1- Ph-L2- group replacing one of the
hydrogens on the amino terminus wherein L1 and L2

(ix) FEATURE:
(A) NAME/KEY: Modified-site
(B) LOCATION: 3
(D) OTHER INFORMATION: /note="(cont) are each a carbonyl
wherein L1 is bound to the peptide fragment
containing the modified sites at locations 1-2 "

(ix) FEATURE:
(A) NAME/KEY: Modified-site
(B) LOCATION: 3
(D) OTHER INFORMATION: /note="(cont)and L2 is bound to
the peptide fragment containing the modified site
at location 4 and Ph is a p-phenylene group."

(ix) FEATURE:
(A) NAME/KEY: Modified-site
(B) LOCATION: 4
(D) OTHER INFORMATION: /note="Xaa is a phenylalanine analog having a -CF3 group replacing the hydroxy
of the terminal carboxy."

( x i ) SEQUENCE DESCRIPTION: SEQ ID NO:16:

Xaa Pro Xaa Xaa
1

( 2 ) INFORMATION FOR SEQ ID NO:17:

( i ) SEQUENCE CHARACTERISTICS:
       ( A ) LENGTH: 6 amino acids
       ( B ) TYPE: amino acid
       ( D ) TOPOLOGY: linear ( i i ) MOLECULE TYPE: peptide ( i x ) FEATURE:
       ( A ) NAME/KEY: Modified-site
       ( B ) LOCATION: 1
       ( D ) OTHER INFORMATION: /note="Xaa is a valine analog
          having a - CF2CF3 group replacing the hydroxy of
          the terminal carboxy."

( i x ) FEATURE:
       ( A ) NAME/KEY: Modified-site
       ( B ) LOCATION: 3
       ( D ) OTHER INFORMATION: /note="Xaa is a valine analog
          having a - C(O)- group replacing one of the
          hydrogens on the amino terminus."

( i x ) FEATURE:
       ( A ) NAME/KEY: Modified-site
       ( B ) LOCATION: 6
       ( D ) OTHER INFORMATION: /note="Xaa is a phenylalanine
          analog having the -CF3 group replacing the hydroxy
          of the terminal carboxy."

( x i ) SEQUENCE DESCRIPTION: SEQ ID NO:17:

Xaa Pro Xaa Val Pro Xaa
1               5

( 2 ) INFORMATION FOR SEQ ID NO:18:

( i ) SEQUENCE CHARACTERISTICS:
       ( A ) LENGTH: 6 amino acids
       ( B ) TYPE: amino acid
       ( D ) TOPOLOGY: linear ( i i ) MOLECULE TYPE: peptide ( i x ) FEATURE:
       ( A ) NAME/KEY: Modified-site
       ( B ) LOCATION: 1
       ( D ) OTHER INFORMATION: /note="Xaa is a valine analog
          having a - CF2CF3 group replacing the hydroxy of
          the terminal carboxy."

( i x ) FEATURE:
       ( A ) NAME/KEY: Modified-site
       ( B ) LOCATION: 3
       ( D ) OTHER INFORMATION: /note="Xaa is a valine analog
          having a - (CH2)n+2- group wherein n is 0 replacing
          one of the hydrogens on the amino terminus."

( i x ) FEATURE:
       ( A ) NAME/KEY: Modified-site
       ( B ) LOCATION: 6
       ( D ) OTHER INFORMATION: /note="Xaa is a phenylalanine
          analog having a -CF3 group replacing the hydroxy
          of the terminal carboxy."

( x i ) SEQUENCE DESCRIPTION: SEQ ID NO:18:

Xaa Pro Xaa Val Pro Xaa
1               5